US00PP15740P2

(12) United States Plant Patent
Lim et al.

(10) Patent No.: US PP15,740 P2
(45) Date of Patent: Apr. 26, 2005

(54) SHRUB ROSE PLANT NAMED 'BAINDER'

(50) Latin Name: *Rosa hybrida*
Varietal Denomination: BAInder

(75) Inventors: Peter P. Lim, Yamhill, OR (US); Jerry Twomey, Leucadia, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 39 days.

(21) Appl. No.: 10/812,002

(22) Filed: Mar. 30, 2004

(51) Int. Cl.[7] ..... A01H 5/00
(52) U.S. Cl. ..... Plt./102
(58) Field of Search ..... Plt./102

*Primary Examiner*—Anne Marie Grunberg
*Assistant Examiner*—Annette H Para
(74) *Attorney, Agent, or Firm*—Burns, Doane, Swecker & Mathis, LLP

(57) ABSTRACT

A new and distinct variety of landscape shrub rose plant is provided which forms on a continuous basis attractive double red blended with pink blossoms. The blossoms are borne singly and in loose clusters. The plant exhibits a compact, upright and bushy growth habit, satiny medium green foliage, and excellent tolerance to Black Spot and Powdery Mildew. The attractive medium green foliage contrasts nicely with the red blended with pink blossom coloration. A tough rose plant of good hardiness is provided. The plant can be grown to advantage as a specimen, border planting, or as a mass planting.

2 Drawing Sheets

Botanical commercial classification: *Rosa hybrida*/Shrub Rose Plant.
Varietal denomination: cv. 'BAInder'.

SUMMARY OF THE INVENTION

The new variety of *Rosa hybrida* landscape shrub rose plant was created at Yamhill, Oreg. during 1993 by artificial pollination wherein two parents were crossed which previously had been studied in the hope that they would contribute the desired characteristics. The female parent (i.e., the seed parent) was an unnamed plant designated 4-40A. Such female parent was an unreleased plant from our breeding program and was not available to the public. The male parent (i.e., the pollen parent) was the 'Meipitac' variety (U.S. Plant Pat. No. 7,783). The 'Meipitac' variety is marketed under the CAREFREE WONDER trademark. The parentage of the new variety can be summarized as follows:

4-40A×'Meipatac'.

The seeds resulting from the above pollination were sown and plants were obtained which were physically and biologically different from each other. Selective study resulted in the identification during 1996 of a single plant of the new variety having the distinctive ornamental characteristics hereafter described.

It was found that the new variety of the present invention:

(a) exhibits a compact, upright and bushy growth habit, (b) forms continuously attractive double red blended with pink blossoms, (c) forms satiny medium green adult foliage, (d) displays excellent tolerance to Black Spot and Powdery Mildew; and (e) is particularly well suited for growing as attractive ornamentation in parks and gardens.

The red buds open to the medium red blended with pink blooms that contrast nicely with the medium green foliage.

The official American Rose Society color of the blooms is medium red. A tough shrub rose plant having good hardiness is provided.

The new variety well meets the needs of the horticultural industry. It can be grown to advantage anywhere in the landscape where attractive ornamentation is desired. The distinctive blossoms are displayed throughout the summer on a continuous basis. The plant can be grown as a specimen, border planting, or as a mass ground cover.

The new variety can be readily distinguished from other varieties including its parental varieties. More specifically, the '4-40A' variety forms deep orange double blossoms having approximately 30 petals on average, and the 'Meipitac' variety forms pointed buds and pink double blossoms having approximately 26 petals on average. The 'MORten' variety (U.S. Plant Pat. No. 8,199) forms pointed buds wherein the opening flower is medium red with a lighter red reverse and commonly assumes a greater height of approximately 1.5 m. Such 'MORten' variety sometimes is known as the 'Linda Campbell' variety. The 'Henry Kelsey' variety (non-patented in the United States) forms dark red opening flowers changing to medium red having approximately 28 petals and commonly assumes a greater height of approximately 1.8 m.

The new variety has been found to undergo asexual propagation by budding on an understock beginning in April 1994 and by the rooting of cuttings. 'Dr. Huey' rootstock was used during the budding. Such asexual propagation by these techniques at Yamhill, Oreg., St. Paul, Minn., and at Phoenix, Ariz. has shown that the characteristics of the new variety are stable and are strictly transmissible by such asexual propagation from one generation to another. The new variety grows well on its own roots.

Initially the new plant was designated 93A130-14P. The new variety subsequently has been named the 'BAInder' variety, and currently is being marketed while using the GARDEN JUBILEE and HOT WONDER trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately three years of age, and were being grown outdoors at St. Paul, Minn. during the 2002 season.

DETAILED DESCRIPTION

Figure 1:
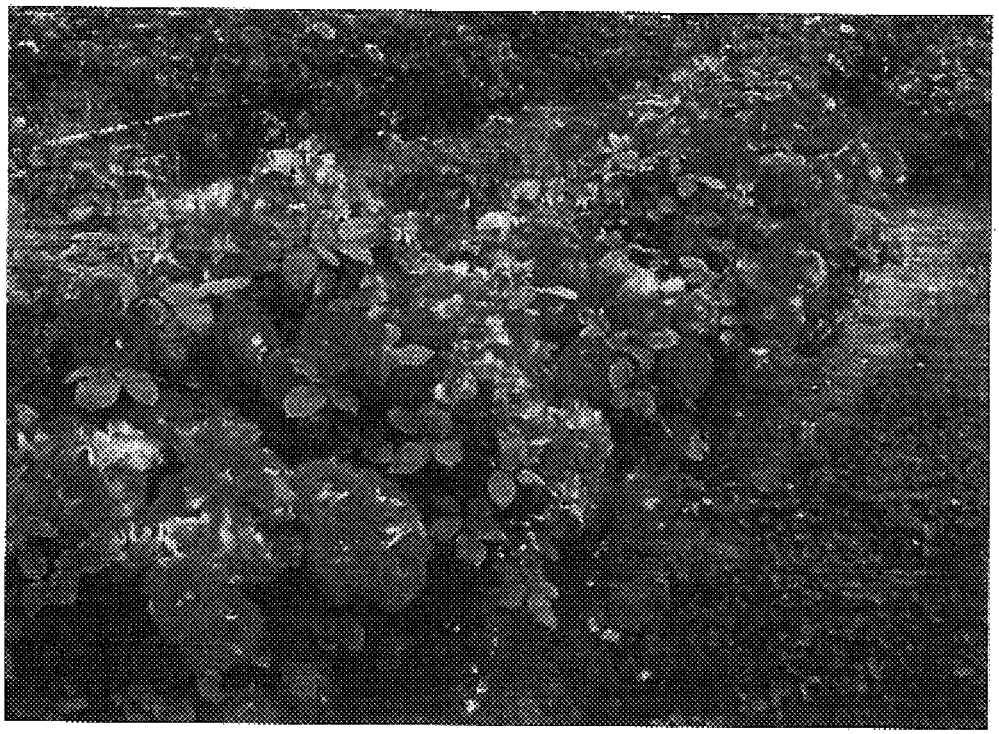
FIG. 1 illustrates a row of typical plants of the new variety while abundantly blooming. The attractive medium foliage also is shown.
Figure 2:
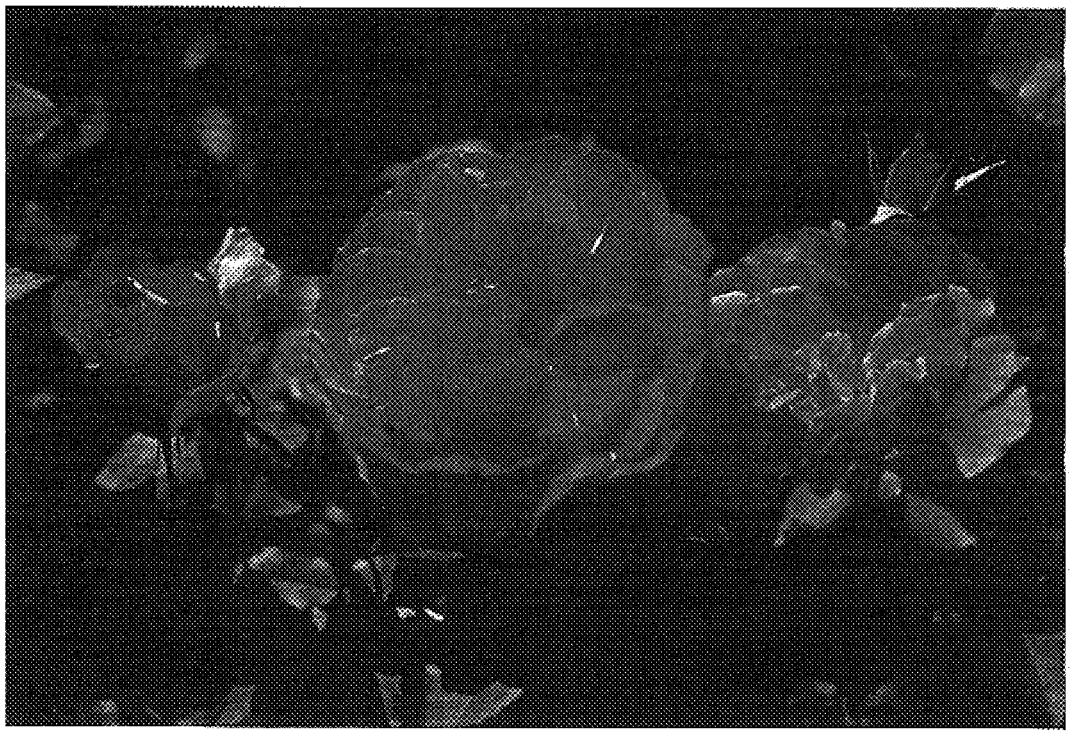
FIG. 2 illustrates a closer view of typical bud and blossoms of the new variety at various stages of opening.
Figure 3:
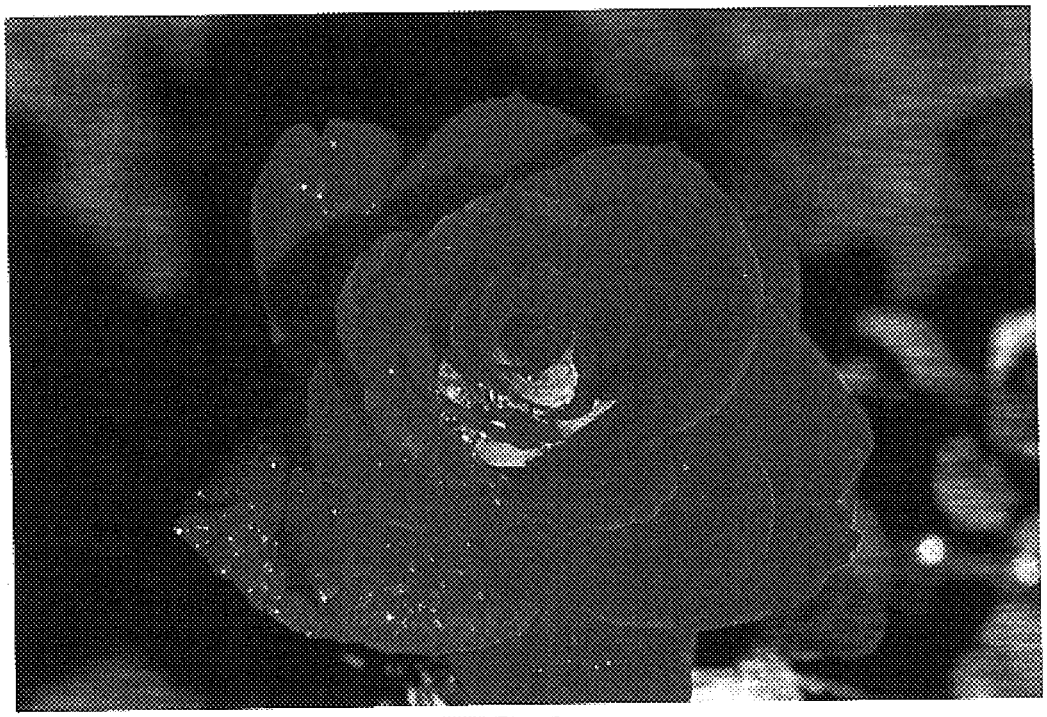
FIG. 3 illustrates a typical open blossom of the new variety wherein the lighter coloration of the under petal surface is apparent at the center of the bloom.
Figure 4:
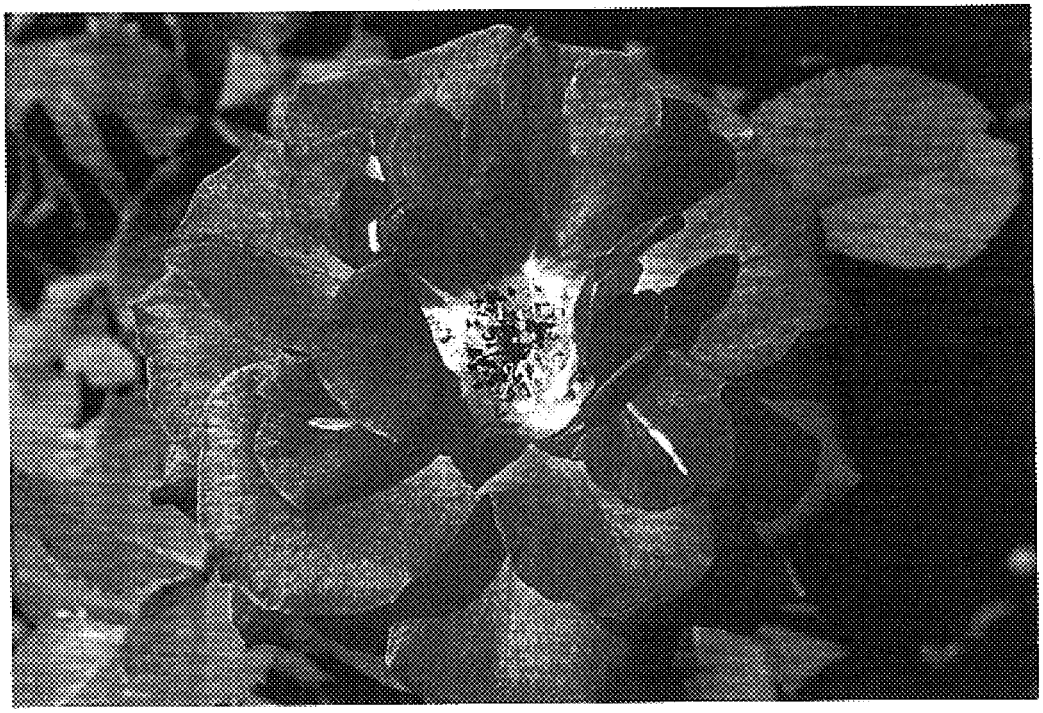
FIG. 4 illustrates a typical fully mature blossom and foliage of the new variety. The yellow basal petal spot and the stamens and pistils also are visible.

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June and July 2002 and 2003 at St. Paul, Minn., and June 2003 at Yamhill, Oreg.

Botanical classification: *Rosa hybrida,* var. 'BAInder'.
Class: Landscape Shrub.
Plant:
- *Height.*—Approximately 90 cm on average at the end of the growing season.
- *Width.*—Approximately 90 cm on average at the end of the growing season.
- *Habit.*—Compact, upright, bushy, and rounded.

Branches:
- *Color.*—Young stems: Yellow-Green Group 143B with some lightening to Yellow-Green Group 143C and 143D. Adult wood: Green Group 137C with some streaking of Greyed-Orange Group 165A and 165B.
- *Thorns.*—Size: commonly approximately 0.75 cm in length on average. Color: Yellow-Green Group 144C with highlights of Greyed-Red Group 180A.

Leaves:
- *Stipules.*—Generally parallel with the auricle facing outward.
- *Petioles.*—Upper surface: Green Group 137C with highlights of Greyed-Purple Group 187B. Under surface: Yellow-Green Group 144C.
- *Leaflets.*—Number: 3, 5, and 7 (most often). Shape: ovate with a rounded base and an acuminate tip. Margin: serrulate. Texture: bear a satiny finish. General appearance: medium green with a satiny surface when mature. Color (young foliage): Upper surface: Greyed-Purple Group 187B with highlights of Green Group 137B. Under surface: Greyed-Purple Group 187B with highlights of Green Group 137C. Color (adult foliage): Upper surface: between Green Group 137A and Yellow-Green Group 147A. Under surface: Green Group 137C with highlights of Greyed-Purple Group 187B at the margin.

Inflorescence:
- *Number of flowers.*—Singly or in loose clusters of commonly up to approximately 5 blossoms. Such bearing is influenced by the environmental conditions.
- *Peduncle.*—Between Green Group 137A and 137B, and the length is approximately 1.3 cm on average.
- *Sepals.*—Upper surface: Green Group 133C with highlights of Greyed-Purple Group 184C and with some pubescence. Under surface: Green Group 143B with highlights of Green Group 143A and Greyed-Purple Group 184B. Size: approximately 2.5 cm in length on average.
- *Buds.*—Shape: oval to slightly pointed. Size: medium. Length: approximately 2.0 cm on average. Diameter: approximately 1.5 cm on average. Color: Upper petal surface: Red-Purple Group 60A and 60B. Under petal surface: Red-Purple Group 63D with highlights of Red-Purple Group 63A and 63B.
- *Flower.*—Shape: double. Diameter: approximately 7.5 cm on average. Color (when opening begins): Upper surface: between Red Group 53B and 53C. Under surface: Red Group 54C blended with Red-Purple Group 57A. Color (when blooming): Upper surface: between Red Group 53C and 53D blended with Red-Purple Group 57A. Under surface: Red Group 55C blended with Red-Purple Group 57A and 57B. Color (at end of blooming): Upper surface: Red-Purple Group 57B and Red-Purple Group 61C. Under surface: Red-Purple Group 62D with highlights of Red-Purple Group 61C. Color (basal petal spot): Yellow Group 2A blended with Yellow Group 4C. Fragrance: slight sweet honey. Lasting quality: the blossoms commonly last approximately 5 to 7 days on average depending upon the temperature and sunlight exposure, and when in a vase approximately 4 to 5 days if cut when the buds are opening. Petal number: approximately 22 under normal growing conditions. Petal shape: wedge-shaped with a curled apex. Petal drop: commonly the petals detach cleanly at full blossom maturity. Anthers: Yellow Group 13A. Filament number: commonly approximately 89 on average. Filament color: Yellow Group 3A. Pistils: approximately 42 on average. Stigmas: Yellow Group 6A in coloration. Styles: Red Group 44A changing to Yellow Group 1C upon full maturity. Receptacle: separate and free. Hip shape: ovoid. Seeds: oval to round, rugose at the apex with villose hairs, and Greyed-Orange Group 166C with highlights of Greyed-Orange Group 165A in coloration.

Development:
- *Vegetation.*—Vigorous.
- *Blooming.*—In abundance in June and continuously thereafter for the remainder of the season.
- *Resistance to diseases.*—Excellent tolerance to Black Spot, and Powdery Mildew.
- *Hardiness zone.*—U.S.D.A. Hardiness Zone Nos. 4 to 9.

We claim:

1. A new and distinct variety of landscape shrub rose plant characterized by the following combination of characteristics:

(a) exhibits a compact, upright and bushy growth habit,
(b) forms continuously attractive double red blended with pink blossoms,
(c) forms satiny medium green adult foliage,
(d) displays excellent tolerance to Black Spot and Powdery Mildew; and
(e) is particularly well suited for growing as attractive ornamentation in parks and gardens;

substantially as herein shown and described.

* * * * *